United States Patent [19]

Peschmann

[11] Patent Number: 4,535,243
[45] Date of Patent: Aug. 13, 1985

[54] X-RAY DETECTOR FOR HIGH SPEED X-RAY SCANNING SYSTEM

[75] Inventor: Kristian R. Peschmann, San Francisco, Calif.

[73] Assignee: Imatron Associates, San Francisco, Calif.

[21] Appl. No.: 476,426

[22] Filed: Mar. 17, 1983

[51] Int. Cl.³ .............................................. G01T 1/20
[52] U.S. Cl. ................................................ 250/363 S
[58] Field of Search .............. 250/361 R, 363 R, 366, 250/367, 368, 369; 307/520, 543; 328/167; 330/107, 109

[56] References Cited

U.S. PATENT DOCUMENTS

| | | | |
|---|---|---|---|
| 3,924,199 | 12/1975 | Pearlman | 330/107 |
| 4,034,223 | 7/1977 | Kowalski | 250/369 |
| 4,292,538 | 9/1981 | Carlson | 250/367 |
| 4,352,021 | 9/1982 | Boyd et al. | 378/10 |

OTHER PUBLICATIONS

*Optical Radiation Measurements*, vol. 4, by W. Budde, 1983, p. 266.

Primary Examiner—Alfred E. Smith
Assistant Examiner—Vincent J. Lemmo
Attorney, Agent, or Firm—Flehr, Hohbach, Test, Albritton & Herbert

[57] ABSTRACT

A high speed multiple section, computed-tomographic X-ray scanner includes a plurality of radiation detectors arranged in two rings. Each detector comprises an elongated scintillator crystal, a small area photodiode positioned at one end of the crystal, and a light reflector positioned at the opposite end of the crystal with the crystal functioning as a light pipe in directing light to the photodiode. An active low pass filter is employed as a preamplifier for current from each photodiode.

5 Claims, 9 Drawing Figures

U.S. Patent    Aug. 13, 1985    Sheet 1 of 4    4,535,243
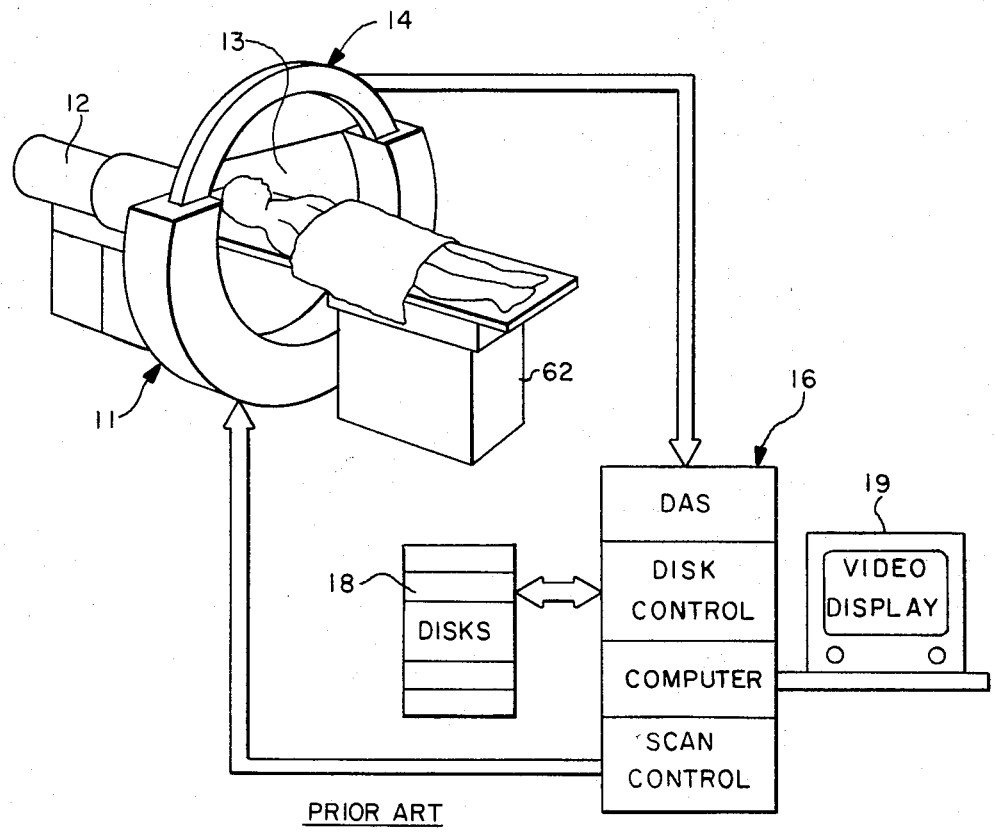
PRIOR ART
FIG.—1
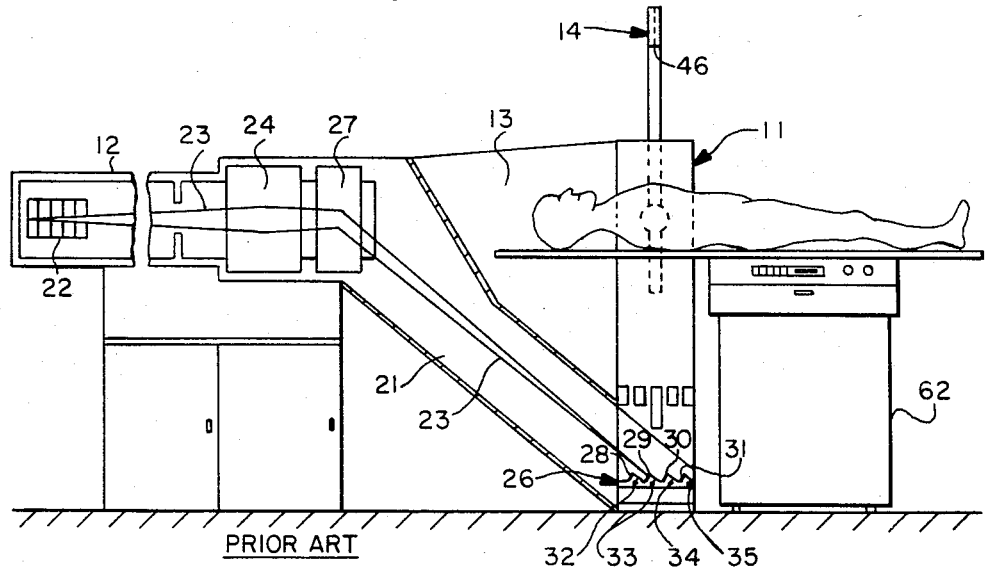
PRIOR ART
FIG.—2

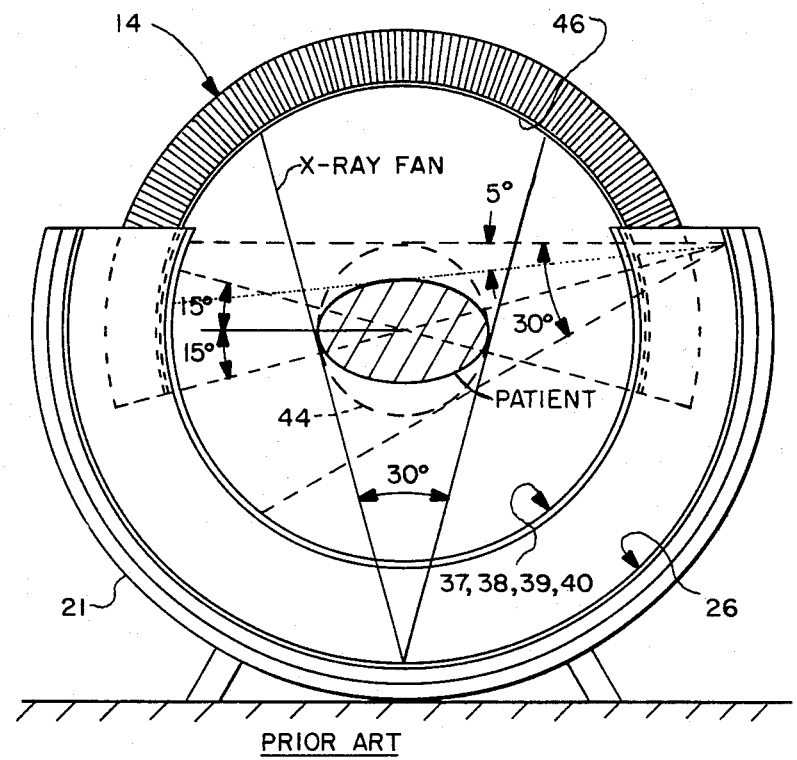
PRIOR ART
FIG.—3
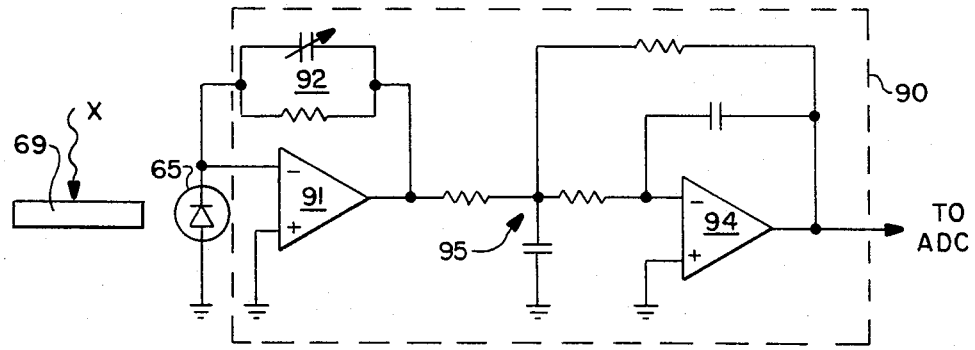
FIG.—8

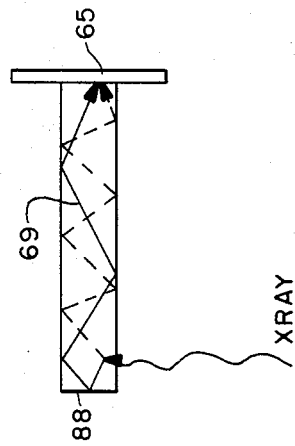
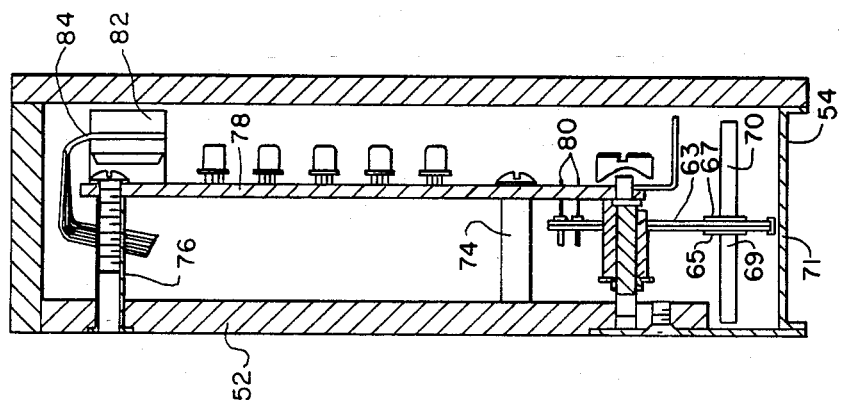
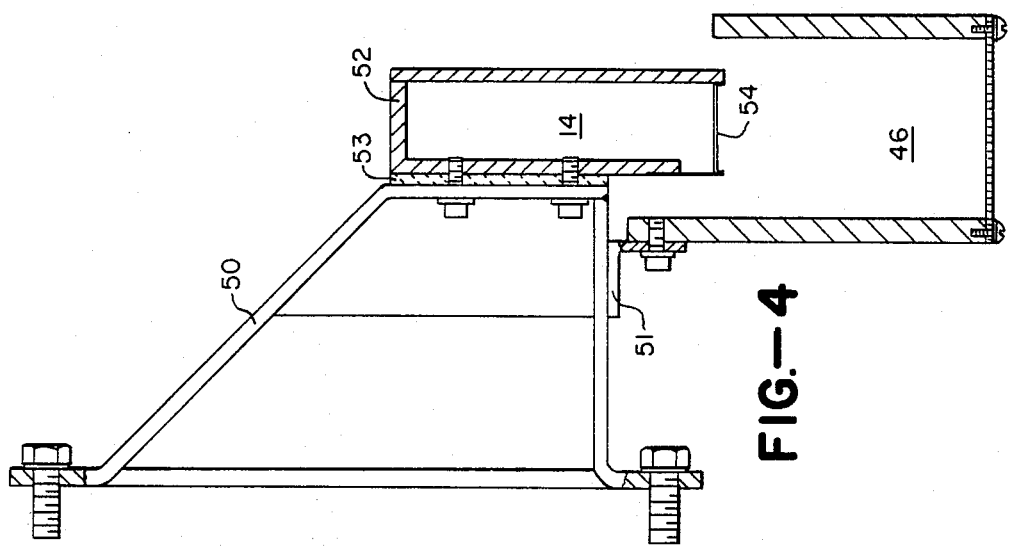
FIG.—6
FIG.—5
FIG.—4

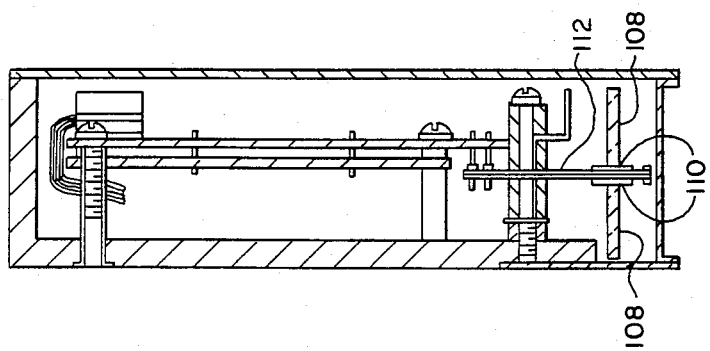
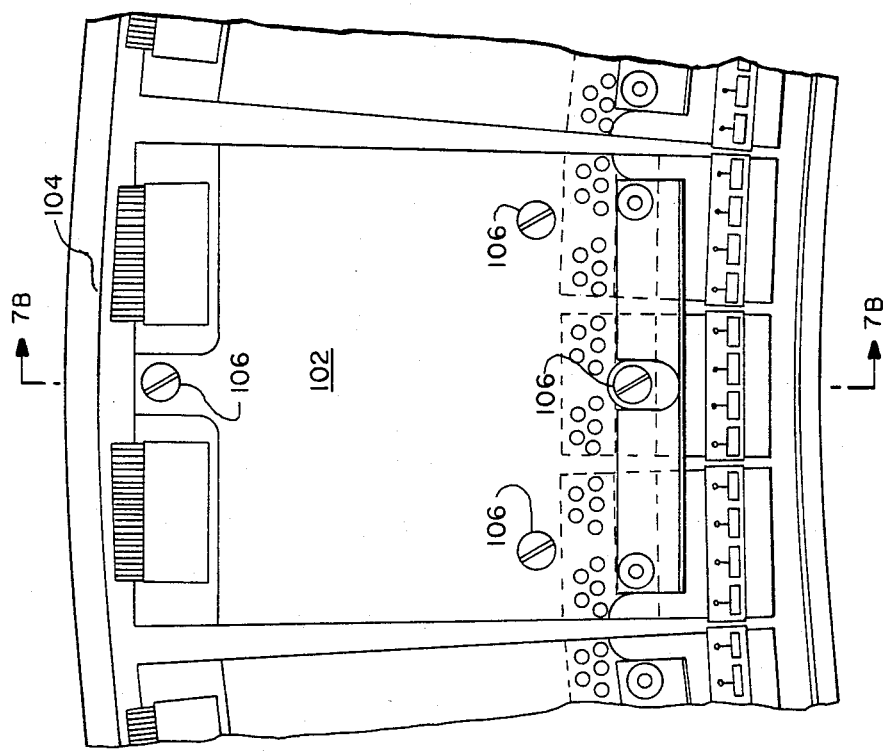
FIG.—7B
FIG.—7A

X-RAY DETECTOR FOR HIGH SPEED X-RAY SCANNING SYSTEM

This invention relates generally to high speed multiple section computed-tomographic (CT) X-ray transmission scanners, and more particularly the invention relates to a detector array which accommodates the high sampling rate in such X-ray scanners.

Disclosed in U.S. Pat. No. 4,352,021 is a high speed X-ray scanning system in which the X-ray source and the X-ray detectors are stationary and a plurality of fan beams of radiation is generated by sweeping an electron beam across a plurality of targets arcuately arranged whereby each target generates radiation fan beams.

The electronic scanning system incorporates a single electron beam tube. The electron beam is deflected by suitable magnetic and/or electric fields to produce a movable X-ray source on one of four adjacent semi-circular target rings to provide scanning fan beams that can be used to image an entire volume of tissue in multiple sections. Such an electronic scanning system is vastly superior in speed to the mechanical scanning systems. Fraction-of-a-second scan time of a volume can be achieved as compared to one or more seconds required for the mechanical scan of a single section. The system eliminates the need for moving parts that require high precision and alignment. In addition, elaborate systems of sliding electrical contacts are eliminated. The scanner is an improvement over that shown and described in U.S. Pat. No. 4,158,142 in that it permits nearly simultaneous viewing multiple sections of the body which may encompass a region as large as the heart. The scanner can provide as many as eight sections.

The system employs a plurality of detectors mounted opposite the target rings. The detectors are arranged in two adjacent partial-circular ring arrays. Each of the arrays contains a multiplicity of detectors as, for example, 444 detectors each, providing a total of 888 detectors. The angular separation of two adjacent detectors is in the order of 0.5 degrees resulting in very high resolution. The scanning system is provided with collimators both for the X-ray source and for the detectors. The source collimator provides a fan-shaped beam 30° of which covers the body. The optional detector collimators provide interchangeable options: dual section detector arrays, single section detector arrays and high resolution single section detector arrays. A variety of scanning modes can be selected with up to eight sections being scanned at a rate of at least one scan per second.

Because of the high sampling rate necessary in the multiple section scanner, conventional X-ray detectors do not have the response speed for use therein. The detector and preamplifier must have a high signal bandwidth. U.S. Pat. No. 4,338,521 discloses a modular radiation detector in which scintillator crystals convert radiation to light, and broad area photo-diodes positioned with the crystals convert the light to electrical currents. However, when increasing the bandwidths of existing crystal photodiode detectors, the noise floor which increases with increasing bandwidth limits the sensitivity of the detector with the result that smaller signals are buried in electronic noise and cannot be detected.

Accordingly, an object of the invention is an improved high speed multiple section X-ray transmission scanner.

Another object of the invention is an improved X-ray detector for use in high speed X-ray scanning systems.

A feature of the invention is a small area photodiode and a light pipe for directing light to the small area photodiode.

Another feature of the invention is the use of an active low pass filter in the preamplifier of the detector.

Briefly, an X-ray detector in accordance with the invention includes an elongated scintillator crystal having opposing end surfaces. A small area photodiode is positioned at one end of the crystal, and the opposite end includes a light reflecting surface. The crystal is positioned in the path of radiation, and light generated by the crystal in response to the radiation is directed to the photodiode. In effect, the crystal functions as a light pipe in directing internally reflected light to the diode. Electrical current from the photodiode is applied to a preamplifier and an active filter.

In a preferred embodiment, an array of detectors includes a supporting substrate with a plurality of photodiodes mounted on opposing sides thereof. Scintillator crystals extend outwardly from the diodes in the radiation path. Alternatively, the diodes can be mounted on the ends of the crystals away from the substrate with the crystals mounted directly to the substrate.

The invention and objects and features thereof will be more readily apparent from the following detailed description and appended claims when taken with the drawing, in which:

FIG. 1 is a schematic diagram partly in perspective showing a high speed multiple section computed tomographic X-ray transmission scanning system.

FIG. 2 is a cross section view of a portion of the system of FIG. 1.

FIG. 3 is an end view of the system of FIG. 1.

FIG. 4 is a section view of radiation detectors in accordance with the present invention useful in the system of FIG. 1.

FIG. 5 is an enlarged section view of the detectors of FIG. 4.

FIG. 6 is a section view of a scintillator crystal and photodiode in the array of FIGS. 4 and 5.

FIGS. 7A and 7B are a front elevation and section view, respectively, of a portion of the detectors and illustrating modularity thereof.

FIG. 8 is an electrical schematic of an active filter in the preamplifier of the detector array of FIGS. 4 and 5.

Referring to FIG. 1, the system of U.S. Pat. No. 4,352,021 is seen to include three major components: a scan tube 11 including a cylindrical portion 12, and a partial-circular conical portion 13; a detectory array 14; and, a computer system 16. The scan tube projects an electron beam to target rings which generate X-rays. The X-rays are intercepted by the detector array 14. The output of the detector array is applied to the computer system 16. The computer system includes a plurality of storage discs 18 for recording the data for later processing. The computer system also includes an output which controls the scan tube. A video display 19 presents the data.

Referring more particularly to FIGS. 2 and 3, the scanning system and detection system is shown in more detail. The electron beam tube 11 includes a vacuum envelope 21 which houses an electron gun 22 at the cylindrical end 12. The electron gun projects an axial electron beam 23 along the cylindrical portion. The focus coils 24 focus the beam onto targets 26. Bending coils 27 bend the beam so that it fans out along the partial-circular conical portion of the tube to impinge upon the partial-circular target rings. The target assembly 26 includes a plurality of partial-circular target rings 28, 29, 30 and 31. Suitable cooling coils 32, 33, 34 and 35 are associated with each of the target rings 28, 29, 30 and 31 respectively and serve to cool the target rings.

The bending magnets not only deflect the beam but rapidly sweep it along the partial-circular targets shown in FIGS. 2 and 3. The target rings are scanned serially to obtain a multiple section examination as will be presently described. Ring collimators 37, 38, 39 and 40 are disposed to intercept X-rays emitted by the target rings and define an X-ray beam projected as a one or two centimeter thick planar beam. A fan-shaped sector of this beam is detected by the curved detector array and the measured valves are utilized to reconstruct a tomographic image.

FIG. 4 is a section view illustrating the mounting of the detector array 14 and post patient collimator 46 to a support frame 50 of the scanner system. The collimator 46 is bolted to an angle bar 51 depending from the support frame 50, and above the collimator and in alignment therewith the housing 52 for the detector arrary 14 is bolted to the frame 50 with an electrically insulative spacer 53 positioned therebetween. A window 54 of thin aluminum, for example, seals the housing 52 and the detector array therein.

As noted above, the radiation detectors must have a large bandwidth and fast response speed to accommodate the high sampling rate necessary in the multiple section scanner.

FIG. 5 is an enlarged section view of the housing 52 illustrating the arrangement of detector elements and preamplifier circuitry therein in accordance with one embodiment of the invention. In this view a supporting substrate 63 supports photodiodes 65 and 67 on opposite sides thereof with elongated scintillator crystals 69 and 70 attached to the diodes 65 and 67, respectively, and extending outwardly therefrom in general alignment with the window 54. A heavy metal attachment 71 is placed on the end of board 63 as a shield against radiation. Diode 65 and crystal 69 are part of one detector ring, and diode 67 and crystal 70 are part of the other detector ring.

The supporting substrate 63 is fastened to the support housing 52 by means of bolt 72. Standoffs 74 and 76 extend from the wall of housing 52 and receive the preamplifier board 78 thereon. The photodiodes 65 and 67 are interconnected by printed wiring on the substrate 63 and through feedthrough connectors 80 to the preamplifier and printed circuit board 78. The electrical output from the preamplifier 78 is applied through a connector 82 and cable 84 to the computer system 16 of FIG. 1.

The scintillator crystals 69 and 70 are positioned in alignment with the window 54 to receive collimated radiation. The crystals convert the radiation to light which is then directed to the photodiodes mounted at one end of the crystals. FIG. 6 is an enlarged view illustrating the function of the scintillator crystal 69 as a light pipe for directing light to the photodiode 65 at one end thereof. The opposite end of the crystal is provided with a light reflecting surface 88 such as a layer of aluminum.

Importantly, the diode has a much smaller sensitive area (and less capacitance associated therewith) which is able to receive sufficient optical energy for signal generation due to the concentration of light through the light pipe function of the scintillator crystal 69.

Advantageously, the detector array can be modular in structure for ease in mounting and aligning the detectors and for replacing defective detectors. FIGS. 7A and 7B are a front elevation and section view, respectively, of a portion of the detectors and illustrating the modularity thereof. In FIG. 7A the module 102 is fastened to the support frame 104 by means of bolts 106. The module 102 has two rows of twelve detectors arranged as illustrated in the section view of FIG. 7B taken along the line 7B—7B of FIG. 7A. FIG. 7B is similar to FIG. 5 with the scintillator crystals 108 extending outwardly from diodes 110 affixed to the board 112.

FIG. 8 is a functional block diagram of the active low pass filter and preamplifier 90 which are mounted on board 78. Current from the diode 65, for example, is passed to a first operational amplifier 91 having a resistive capacitive feedback 92 which functions as a current to voltage converter and provides the first real pole of the filter. The output of amplifier 91 is then applied to a second operational amplifier 94 which cooperatively provide two additional filter poles. The output of amplifier 94 is then applied to the analog to digital converter and computer system.

As described above, the electronic noise floor increases with increasing bandwidth of the detector system. At high bandwidth the dominant source of noise is the input voltage noise of the preamplifier stage. Even without an incoming X-ray flux the noise per unit bandwidth at the amplifier output is proportional to the product $$\omega \cdot C_d \cdot V_{nv} \qquad (1)$$

where $\omega$ is the frequency; $C_d$ is the diode shunt capacitance plus input circuit stray capacitance; and $V_{nv}$ is the input voltage noise of the operational amplifier serving as preamplifier in the current-to-voltage conversion circuit configuration.

From this equation it is seen that in order to limit noise at a given high total bandwidth (or $\omega$), $C_d$ and $V_{nv}$ should be as small as possible. The value of $C_d$ has a lower limit given by silicon technology and the small photodiode area. $V_{nv}$, the input voltage noise of an operational amplifier is likewise finite because of technological reasons. It is known that a conventional switched linear integrator circuit in a CT detector can be replaced by an expotential averaging circuit to present a simplification in terms of reduced complexity of the electronic circuitry.

The averaging circuit is realized by using low-pass networks as in FIG. 8. The first (and real) pole is generated by using a capacitor with the feedback resistor of the first stage (current-to-voltage convertor) and by using an active double complex pole as a second stage. In addition to the averaging function the filter also strongly attenuates the high frequency parts of the noise spectrum without much attenuation of the frequencies containing the information which is needed for the CT-image reconstruction. It is this optimization of the noise attenuation versus information retaining trade-off which renders the multi-complex pole filter approach described here superior to the prior art such as E. A.

Olson, C. R. Smith and D. J. Pisano, RC Filter Versus Integrator Data Collection Circuits for Computed Tomography, *Medical Physics,* 9, (1982), pgs. 69-78. An active filter with even more poles (real and complex) can be used, e.g. 4 poles, 5 poles, 6 poles filter circuits as described by Don Lancaster, Active Filter Cookbook, Howard W. Saums & Co., Inc., Indianapolis, USA.

There has been described a radiation detector having sufficient response speed for use in a multiple section scanner of the described type. While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. An X-ray detector for use in a high speed radiation scanning system comprising an elongated scintillator crystal having two opposing ends, a photodiode, means attaching said photodiode to one end of said crystal, reflection means on the opposite end of said crystal whereby said crystal functions as a light pipe in directing light to said photodiode, and an active low pass filter and amplifier means connected to said photodiode for amplifying electrical signals from said photodiode, said active low pass filter and amplifier means comprising a first operational amplifier having a first filter pole and a second operational amplifier having two filter poles.

2. An X-ray detector array module for use in a high speed radiation scanning system comprising a support substrate having two major surfaces, at least one photodiode mounted on one major surface and at least one photodiode mounted on the other major surface, and a plurality of scintillator crystals, each scintillator crystal being elongated with two opposing ends, each photodiode being positioned in juxtaposition with one end of a scintillator crystal, and reflection means provided on the opposing end whereby said scintillator crystal functions as a light pipe in directing light to a photodiode.

3. The X-ray detector array module as defined by claim 2 and further including a plurality of active low pass filter and amplifier means each connected to a photodiode for amplifying electrical signals from said photodiode.

4. An apparatus for obtaining an X-ray absorption distribution of an object comprising
an evacuated envelope having a longitudinal axis, said envelope including a cylindrical end portion and a conical partial-circular end portion,
an electron gun disposed axially at the cylindrical end and projecting an electron beam,
a focus coil disposed at the cylindrical portion to receive and focus said beam,
bending coils following the focusing coil adapted to receive said beam and direct it into the conical end section and scan the beam along the segment of a circle,
a plurality of adjacent target rings disposed at the end of said conical section to receive said electron beam and generate X-rays in response thereto,
a source collimator adjacent each of said target rings to intercept said X-ray and form a fan-shaped X-ray beam which rotates as the electron beam is moved along the corresponding target ring whereby to form a plurality of fan-shaped X-ray beams to scan a plurality of adjacent sections, at least one for each target ring,
a plurality of detector modules mounted opposite the target ring, said modules arranged to form an array which is a segment of a circle, each module comprising
a support substrate having two major surfaces, at least one photodiode mounted on one major surface and at least one photodiode mounted on the other major surface, and a plurality of scintillator crystals, each scintillator crystal being elongated with two opposing ends, each photodiode being positioned in juxtaposition with the one end of a scintillator crystal, and reflection means provided on the opposing end whereby said scintillator crystal functions as a light pipe in directing light to a photodiode, and
detector collimators serving to direct the beam onto selected ones of said detectors for each target ring.

5. The apparatus as defined by claim 4 wherein each detector further includes an active low pass filter and amplifier means connected to said photodiode for amplifying electrical signals from said photodiode.

* * * * *